(12) United States Patent  
Szelewski et al.

(10) Patent No.: US 7,117,103 B2  
(45) Date of Patent: Oct. 3, 2006

(54) RAPID AUTOMATIC TARGET COMPOUND CONFIRMATION USING DECONVOLUTION AND SPECTRAL MATCHING

(75) Inventors: Michael Joseph Szelewski, Hockessin, DE (US); Elmer Anthony Axelson, Landenberg, PA (US); Chin-Kai Meng, Hockessin, DE (US)

(73) Assignee: Agilent Technologies, Inc., Loveland, CO (US)

( * ) Notice: Subject to any disclaimer, the term of this patent is extended or adjusted under 35 U.S.C. 154(b) by 86 days.

(21) Appl. No.: 10/859,843

(22) Filed: Jun. 3, 2004

(65) Prior Publication Data

US 2005/0273276 A1    Dec. 8, 2005

(51) Int. Cl.  
    *G06F 19/00* (2006.01)
(52) U.S. Cl. ........................................ 702/30
(58) Field of Classification Search .............. 702/30, 702/32, 19; 250/282; 95/8; 435/6, 7; 514/12; 376/107; 455/526; 708/624; 230/281  
See application file for complete search history.

(56) References Cited

U.S. PATENT DOCUMENTS

| 6,104,027 | A  | * | 8/2000 | Gee et al. ................... 250/282 |
| 2003/0229451 | A1 | * | 12/2003 | Hamilton et al. ............. 702/19 |
| 2004/0195500 | A1 | * | 10/2004 | Sachs et al. ................ 250/282 |

OTHER PUBLICATIONS

Merriam-Webster's dictionary, Tenth edition 1993, p. 218, 253, 294 and 375.*

* cited by examiner

*Primary Examiner*—John Barlow  
*Assistant Examiner*—Tung Lau  
(74) *Attorney, Agent, or Firm*—Michael J. Tempel

(57) ABSTRACT

A method for automatically verifying the existence of a target compound comprises generating a total ion chromatogram. The total ion chromatogram comprises a plurality of peaks, each peak representing one or more compounds in a sample matrix, each peak comprising at least two compounds. The method also comprises deconvoluting each peak to isolate each target compound present in the peak, and automatically verifying the identity of each target compound against a target compound library.

16 Claims, 9 Drawing Sheets

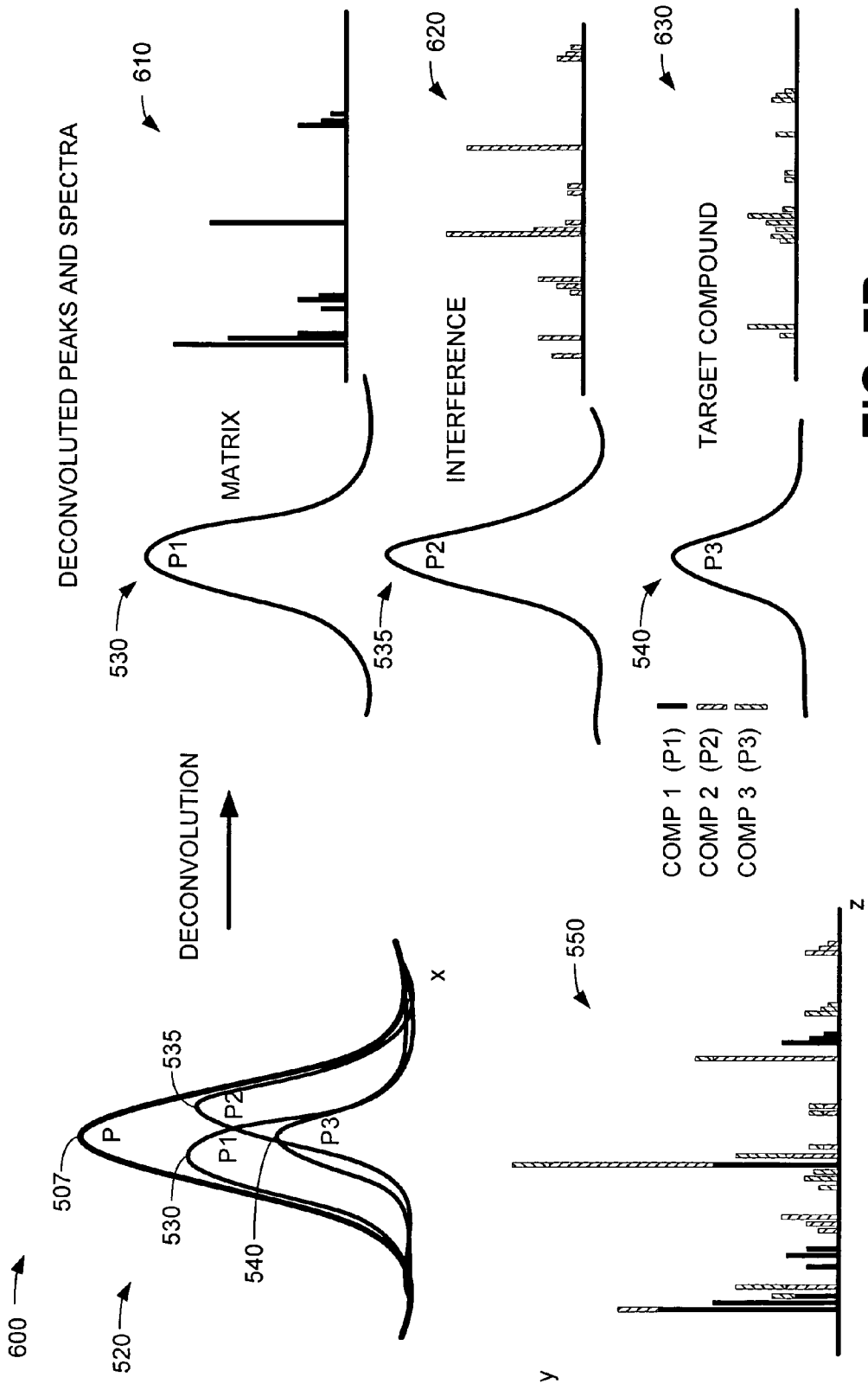

RAPID AUTOMATIC TARGET COMPOUND CONFIRMATION USING DECONVOLUTION AND SPECTRAL MATCHING

BACKGROUND

A gas chromatograph/mass spectrometer (typically abbreviated as "GC/MS") analyzes a sample of material to determine the constituent compounds thereof. For example, a GC/MS can be used to determine the compounds that are in a sample of food. In one application, a GC/MS analyzes food products to detect the presence of contaminants, such as a pesticide, a chemical warfare agent (CWA), or other contaminants present in the sample. The sample is also referred to as a "matrix" or "sample matrix." Typically, a GC/MS analyzes a sample using both time-based parameters (for example, identifying a target compound based on a time window, referred to as "retention time") and on mass-to-charge ratio, referred to as "m/z," that identifies ions present in the target compound. For a sample having multiple components, the GC/MS outputs a signal that is represented by a pulse train having multiple peaks. The position of each peak relates to the identity of the components in the mixture while the area of the peak relates to the quantity (also referred to as abundance) of that component in the mixture.

When a target compound is detected in the sample matrix, the identity of the target compound must be verified. Verification of the target compound is typically automated, but manual review of the analysis results is required to validate the results.

Typically, a number of different software programs may be used to process the results of the analysis performed by the GC/MS. A first program can be used to analyze the results of the GC portion of the GC/MS and to analyze the results of the MS portion of the GC/MS. A second program may be used to confirm the results by comparison with a known database.

Typically, an analyst who must be proficient in the use of the above-mentioned software may require on the order of 20–30 minutes to perform peak averaging and background subtraction to confirm a target compound found by a retention time window analysis and four (4) ion identification. Unfortunately, this confirmation process is time consuming and burdensome, due to matrix interferences. As known by those skilled in the art, matrix interferences are those compounds present in a sample in which one is not interested. They have similar retention times and/or similar ion fingerprints that obscure correct identification of the compounds in which one is interested, which are referred to as the target compounds.

Therefore, it would be desirable to automate the identification and verification of a target compound detected in a sample.

SUMMARY OF THE INVENTION

The invention provides a system and method for automatically identifying a target compound. In one embodiment, a method for automatically identifying a target compound comprises generating a total ion chromatogram. The total ion chromatogram comprises a plurality of peaks, each peak representing one or more compounds in a sample matrix. The method also comprises deconvoluting each peak to isolate each compound present in the peak, and automatically verifying the identity of each compound against a target compound library.

Other systems, methods and advantages in addition to or in lieu of the foregoing are provided by certain embodiments of the invention, as is apparent from the description below with reference to the following drawings.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

FIGS. 7A and 7B are a graphical representation collectively illustrating the deconvolution of the peak "P" of FIG. 6B into its constituent compounds.

DETAILED DESCRIPTION OF THE INVENTION

Figure 1:
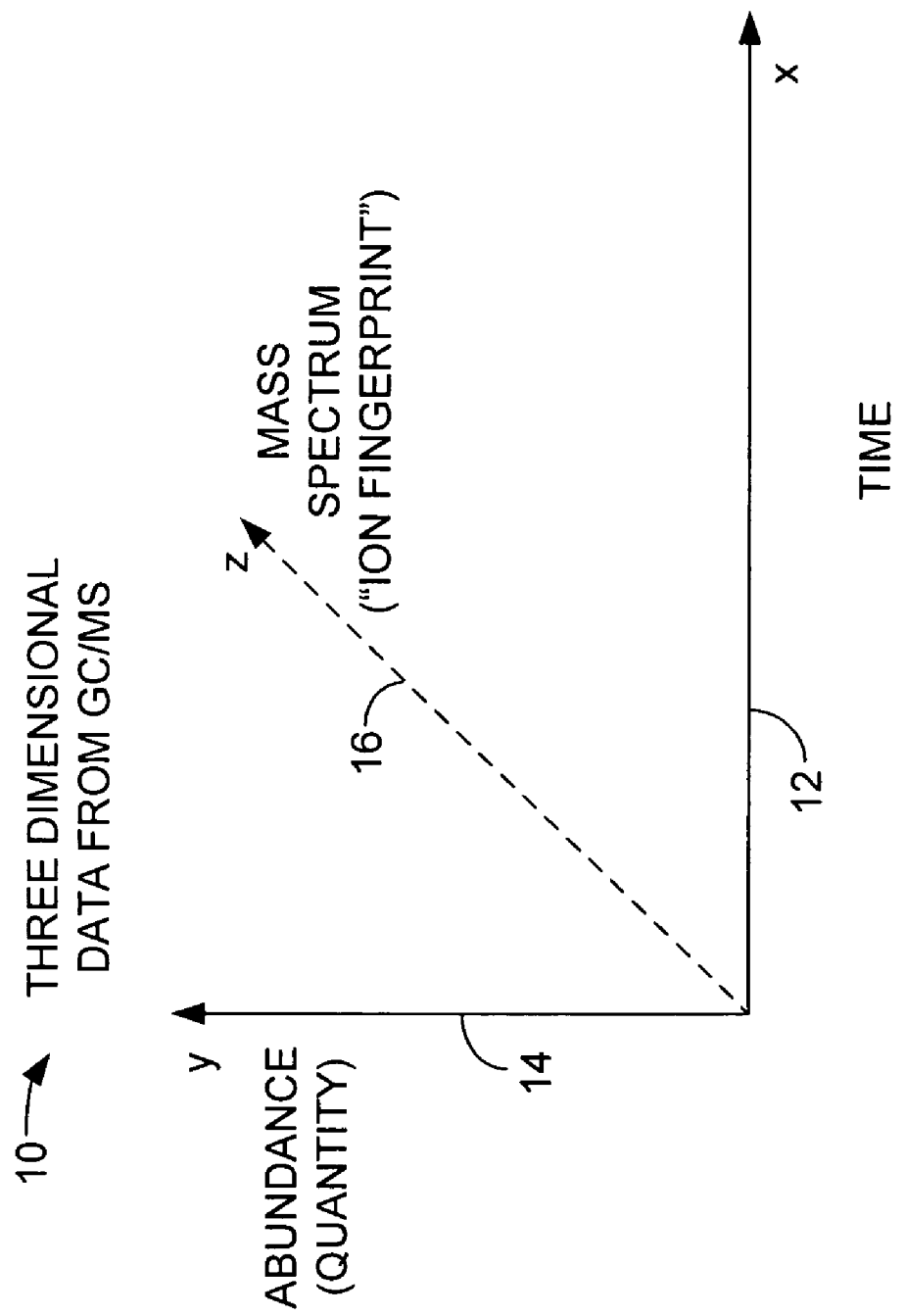
FIG. 1 is a graphical view illustrating the data provided from a gas chromatograph/mass spectrometer (GC/MS).

FIG. 1 is a graphical view illustrating the data provided from a gas chromatograph/mass spectrometer (GC/MS). The graph 10 includes a horizontal axis 12 representing time and a vertical axis 14 representing quantity, or abundance, of a compound detected and identified in a sample matrix. The z axis 16 represents the mass spectrum, also referred to as the "ion fingerprint" of the compound identified from the sample matrix. The data provided from the GC/MS are three dimensional. The x, y and z axes are used to completely identify a compound in a sample matrix. The GC portion of the GC/MS resolves compounds with respect to time while the MS portion of the GC/MS detects resolved components based on a mass spectrum of each component.

Ideally, every compound has a unique mass spectrum by which it can be identified. However, many compounds have similar structures, so their mass spectra are similar. To aid in compound identification, a GC is first used to attempt to separate similar compounds with respect to time. For example, different compounds in a sample matrix resolve differently based on what is referred to as "retention time." The retention time of a compound can be identified by a GC and can be used to preliminarily identify a compound. After the GC portion of a GC/MS identifies compounds in a sample matrix according to retention time, a mass spectrum of the compound, or compounds, is generated by the MS portion of the GC/MS. A complete mass spectrum of a compound can contain from one (1) to hundreds of ions. The exact number of ions that can be used is not exact.

A mass spectrum can comprise a single ion, if that's all the system is configured to search for. Alternatively, if the system is configured to search for all ions, a mass spectrum can contain 50 or 100 or 150+ ions. The number of ions depends on the compound being analyzed. However, due to the availability of processing resources, such as the speed and memory capacity of a processor located in a computing system, it is generally impractical to analyze all of the possible ions. Therefore, in this example, and in a typical GC/MS, a subset of ions, in this example four (4), are analyzed to confirm the existence of a target compound. Using retention time and four ion analysis, a target compound, which is (are) one or more compounds from a subset of all compounds in the universe, can be identified. A different number of ions can be analyzed, depending on the application. By identifying a target compound first using the retention time of a target compound using the GC portion of the GC/MS, and then by using the MS portion of the GC/MC to perform the ion analysis, a reasonably certain analysis identifying the target compound in the sample can be obtained. These analyses are combined by the GC/MSD software (to be described below) to produce a first "result." The first result is generated from what is referred to as a total ion chromatogram (TIC), which will be described in FIG. 2.

The TIC can then be supplied to a software program, referred to as the Automated Mass Spectral Deconvolution and Identification Software (AMDIS), to be described below, that is used to deconvolute compounds and compare the resultant deconvoluted mass spectra to a database of known target compound spectra. This produces a second result, and a list of possible target compounds found. The results (deconvoluted mass spectra) are then supplied to a database containing a different set of mass spectra for comparison. Such a database is referred to as the NIST02 library and contains a library of target compounds. The NIST02 library is available from the National Institute of Standards and Technology (NIST) and is generated using all ions. The NIST02 database can be used to verify the identity of a target compound identified using the GC/MS as described above, thus generating a third result. A shortcoming of the above-described identification procedure is that to completely verify the identity of the target compound, the three results must be manually analyzed by an individual familiar with all three procedures and the associated software.

Figure 2:
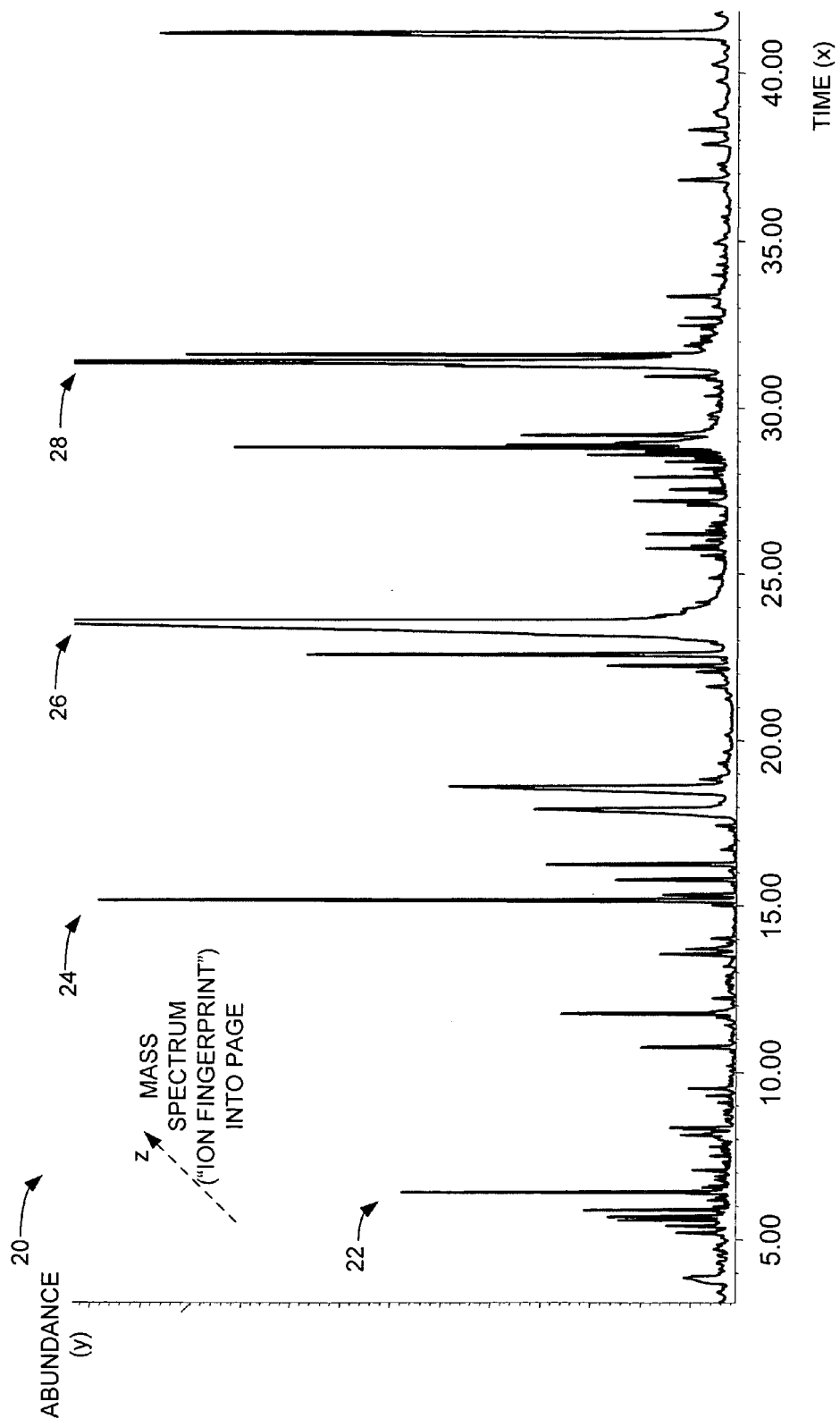
FIG. 2 is a graphical view illustrating a "total ion chromatogram" (TIC) of a sample, including one or more compound(s) plus the sample matrix.

FIG. 2 is a graphical view illustrating a "total ion chromatogram" (TIC) 20 of a sample, including one or more target compounds plus the sample matrix. The horizontal axis corresponds to time, while the vertical axis corresponds to the quantity, or abundance, of a compound in the sample matrix. In FIG. 2, the z axis, which represents the mass spectrum of a compound extends into the page. The total ion chromatogram 20 includes a plurality of peaks, exemplary ones of which are illustrated using reference numerals 22, 24, 26 and 28. Each peak represents one or more compounds, which are identified by the gas chromatograph, in the sample matrix based on retention time (shown on the horizontal axis). The characteristic "ion fingerprint" of each peak, which is not directly shown in FIG. 2, corresponds to the mass spectrum of each of the peaks 22, 24, 26 and 28.

Figure 3:
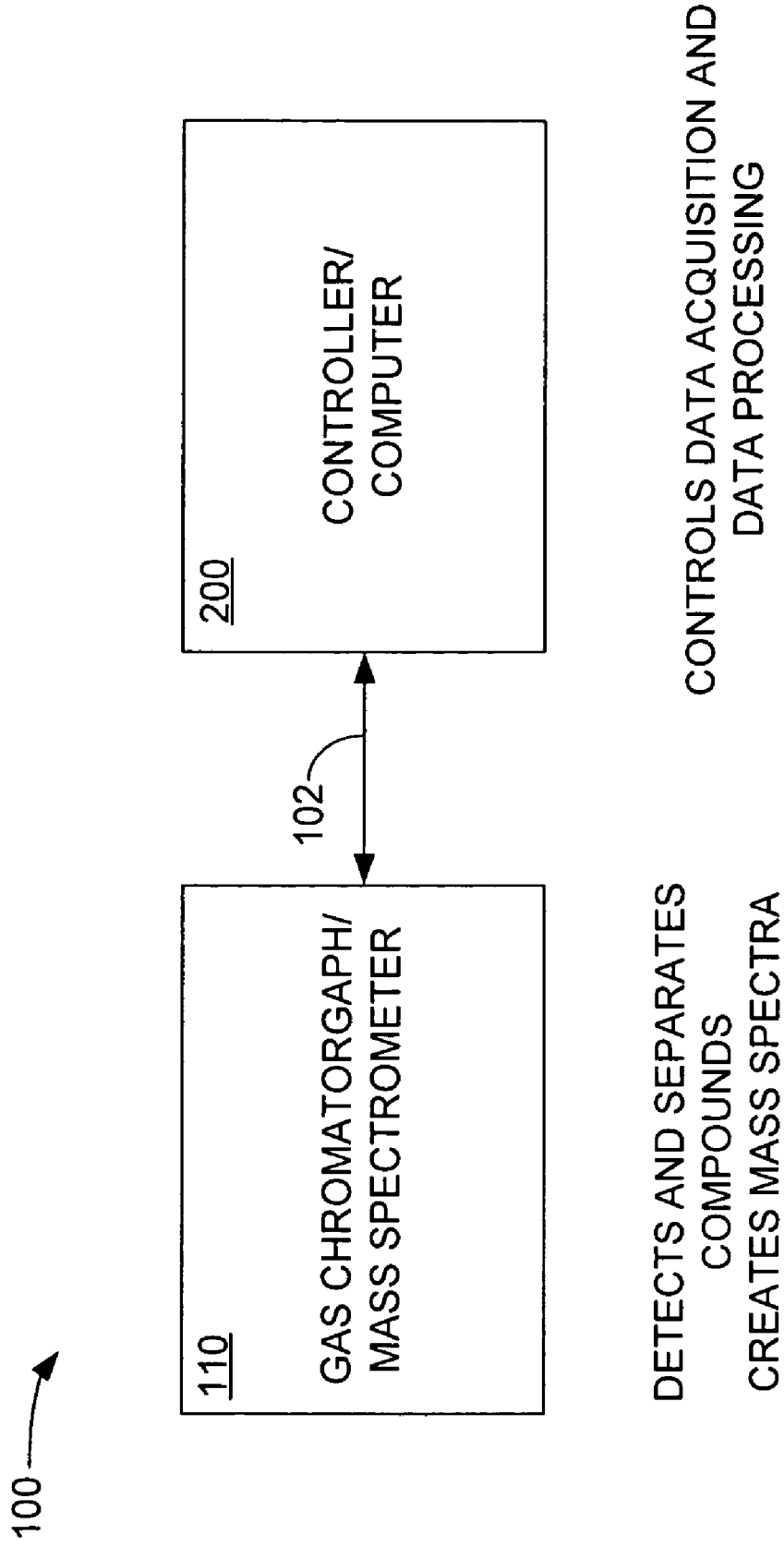
FIG. 3 is a block diagram illustrating a system including a GC/MS and a controller/computer.

FIG. 3 is a block diagram illustrating a system 100 including a GC/MS 110 and a controller/computer 200. The GC/MS 110 is coupled to the controller/computer 200 by a bi-directional connection 102. The GC/MS 110 separates and detects compounds in a sample matrix, as described above, and creates retention time data and mass spectra for each compound. The controller/computer 200 controls data acquisition and data processing relating to the GC/MS 110. The controller 200 can be, for example, a computer, a computerized controller, or other type of computing device that includes processing, interface, and software components that are used to control all aspects of the GC/MS 110. Alternatively, the functionality of the controller/computer 200 can be located in the GS/MS110.

Figure 4:
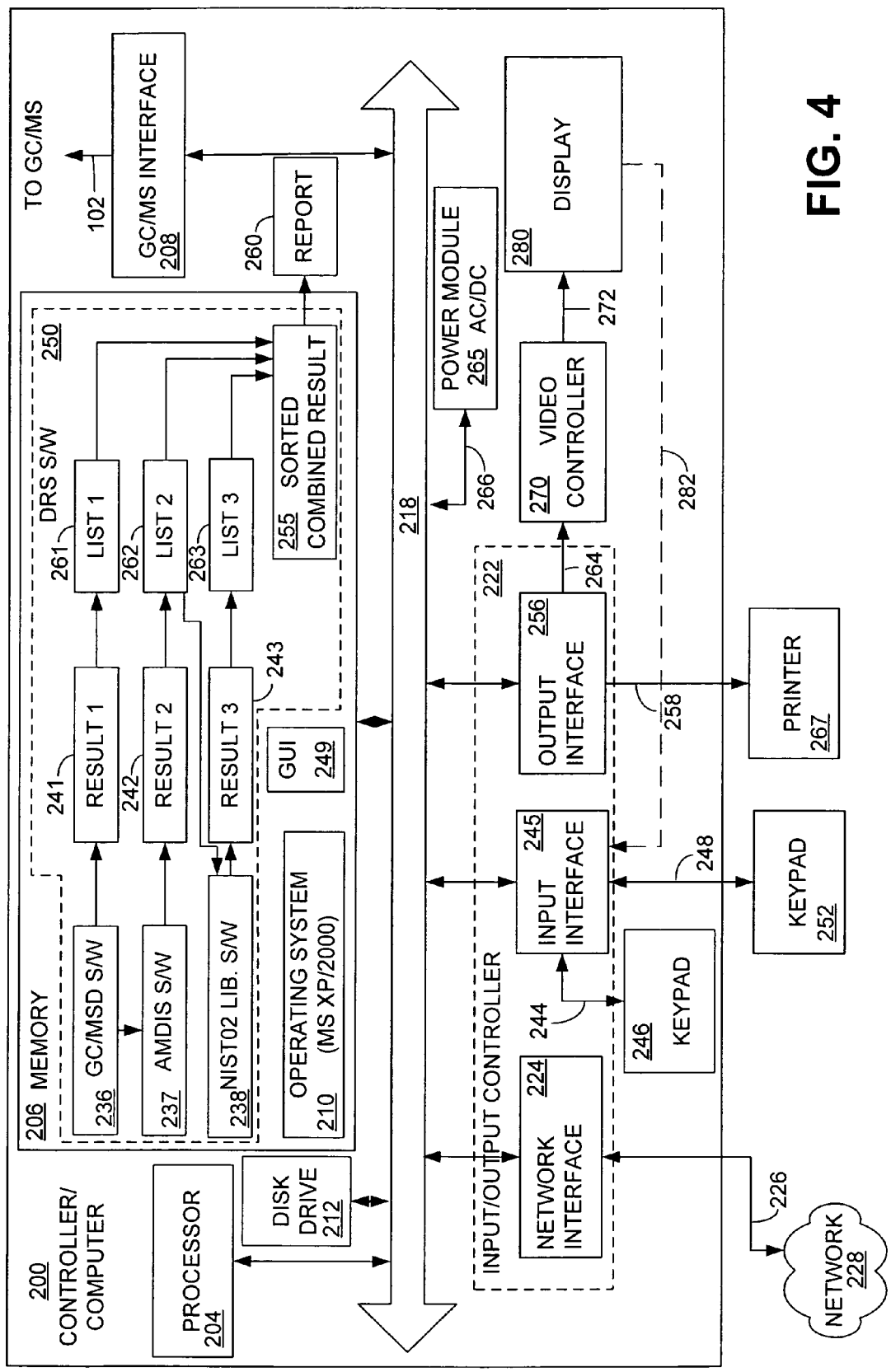
FIG. 4 is a block diagram illustrating an exemplary controller/computer constructed in accordance with an embodiment of the invention.

FIG. 4 is a block diagram illustrating an exemplary controller/computer 200 constructed in accordance with an embodiment of the invention. Generally, in terms of hardware architecture, as shown in FIG. 4, the computer 200 includes a processor 204, memory 206 (one or more random access memory (RAM) elements, read only memory (ROM) elements, etc.), an optional removable media disk drive 212, a gas chromatograph/mass spectrometer interface 208, referred to as a "GC/MS interface 208," an input/output controller 222 and a power module 265 that are connected together and that communicate with each other via a local interface 218. The local interface 218 can be, for example but not limited to, one or more buses or other wired or wireless connections, as is known to those having ordinary skill in the art. The local interface 218 may have additional elements, which are omitted for simplicity, such as buffers (caches), drivers, and controllers, to enable communications. Further, the local interface 218 includes address, control, and data connections to enable appropriate communications among the aforementioned components.

The processor 204 is a hardware device for executing software that can be stored in memory 206. The processor 204 can be any suitable processor for implementing the functionality of the controller/computer 200. In one embodiment, the controller/computer 200 executes on a personal computer (PC).

The memory 206 can include any one or a combination of volatile memory elements (e.g., random access memory (RAM, such as DRAM, SRAM, etc.)) and nonvolatile memory elements (e.g., NVRAM, ROM, hard drive, tape, CDROM, etc.). Moreover, the memory 206 may incorporate electronic, magnetic, optical, and/or other types of storage media. Note that the memory 206 can have a distributed architecture, where various components are situated remote from one another, but can be accessed by the processor 204.

The software in memory 206 may include one or more separate programs, each of which comprise one or more code segments, which are an ordered listing of executable instructions for implementing logical functions. In the example of FIG. 4, the software in the memory 206 includes software in the form of gas chromatograph/mass selective detector (GC/MSD) software 236 (the term "mass selective detector" is synonymous with the term "mass spectrometer"), AMDIS software 237 and NIST02 library software 238. The GC/MSD software 236 can be, for example, a proprietary software module that performs the GC/MS analysis described above using retention time analysis and four ion mass spectra analysis. The AMDIS software 237 can be, for example, compound identification software available from the National Institute of Standards and Technology (NIST). The AMDIS software 237 uses all ions to separate, also referred to as "deconvolute," co-eluting compounds detected by the GC/MSD software 236. Co-eluting compounds are those compounds that have similar retention times when they are analyzed by the GC/MS. The NIST02 library software 238 is also available from the National Institute of Standards and Technology and includes a library of mass spectra formed using all ions.

The GC/MSD software 236 generates a first result 241, including the results of the GC/MS analysis of the sample matrix. The first result can be generated from the information contained in the TIC 20 of FIG. 2. The GC/MSD software 236, under the control of the deconvolution reporting software (DRS) 250, supplies the first result to the AMDIS software 237, which generates a second result 242, further identifying/confirming the identity of the target compounds in the first result 241. The second result 242 is supplied to the NIST02 library software 238, which generates a third result 243 further confirming the identity of the target compounds.

The memory 206 also includes a graphical user interface (GUI) 249. The GUI 249 provides a graphical user interface for the controller/computer 200 and also displays information to a user on the display 280. The memory also includes deconvolution reporting software 250. The deconvolution reporting software 250 generates a first list 261 corresponding to the first result 241, a second list 262 corresponding to the second result 242, and a third list 263 corresponding to the third result 243. The deconvolution reporting software 250 combines the data from the GC/MSD software 236, AMDIS software 237 and the NIST02 library software 238 and generates a sorted combined result 255. The deconvolution reporting software 250 then generates a report 260 for display on the display 280. The deconvolution reporting software 250 generates the sorted combined result by, for example, sorting the lists 261, 262 and 263 based on retention time and/or based on a chemical abstracts service number (CAS #). A CAS number is a unique, universally recognized number assigned to each target compound.

The memory 206 also includes one or more operating software modules, collectively referred to as operating system (O/S) 210. The O/S 210 may include software modules that perform some of the functionality of the controller/computer 200 not specifically described herein.

In a preferred embodiment, the O/S 210 is the commonly available Microsoft 2000 or XP operating system available from Microsoft. However, other operating systems may be used. The operating system 210 essentially controls the execution of other computer programs, such as the GC/MSD software 236, AMDIS software 237, NIST02 software 238 and the deconvolution reporting software 250. The processor 204 and operating system 210 define a computer platform, for which application programs, such as the GC/MSD software 236, AMDIS software 237, NIST02 software 238 and the deconvolution reporting software 250, are written in higher level programming languages. The GC/MSD software 236, AMDIS software 237, NIST02 software 238 and the deconvolution reporting software 250 include the executable instructions that allow the controller/computer 200 to detect, separate and rapidly and automatically identify target compounds in a sample matrix.

The input/output controller 222 includes a network interface 224, an input interface 245 and an output interface 256 each in communication with the local interface 218. The network interface 224 couples the controller/computer 200 to an external network 228 via connection 226. The external network can be any network to which the controller/computer 200 may couple to exchange information. The input interface 245 is coupled to an internal keypad 246 via connection 244 and to an external keypad 252 via connection 248. The internal keypad 246 is located on the controller/computer 200 while the external keypad 252 is an auxiliary keypad to which the controller/computer 200 may be coupled.

The output interface 256 is coupled to a printer 267 via connection 258. The printer 267 can be used to provide a permanent record of the analysis results obtained by the controller/computer 200. The output interface 256 also couples to a video controller 270 via connection 264. The video controller 270 couples to a display 280 via connection 272. The display 280 can be an LCD touch screen display capable of receiving input from a user, but may be any type of suitable display.

The disk drive 212 can be any storage element or memory device, and as used herein, generally refers to flash memory, sometimes referred to as compact flash (CF) or PC card.

The power module 265 can power the controller/computer 200 from an AC power source, or can include batteries and a built in charger to provide portable DC power. The GC/MS 208 provides both electrical and mechanical interfaces to a GC/MS device.

When the controller/computer 200 is in operation, the processor 204 is configured to execute software stored within the memory 206, to communicate data to and from the memory 206 and to generally control operations of the controller/computer 200 and the GC/MS 110 (FIG. 3) pursuant to the software.

When portions of the controller/computer 200 are implemented in software, as is shown in FIG. 4, it should be noted that the O/S 210, GC/MSD software 236, AMDIS software 237, NIST02 software 238 and the deconvolution reporting software 250 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The O/S 210, GC/MSD software 236, AMDIS software 237, NIST02 software 238 and the deconvolution reporting software 250 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device.

The computer readable medium can be, for example but not limited to, an electronic, magnetic, optical, electromagnetic, infrared, or semiconductor system, apparatus, device, or propagation medium. More specific examples (a non-exhaustive list) of the computer-readable medium include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The hardware components of the controller/computer 200 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 5:
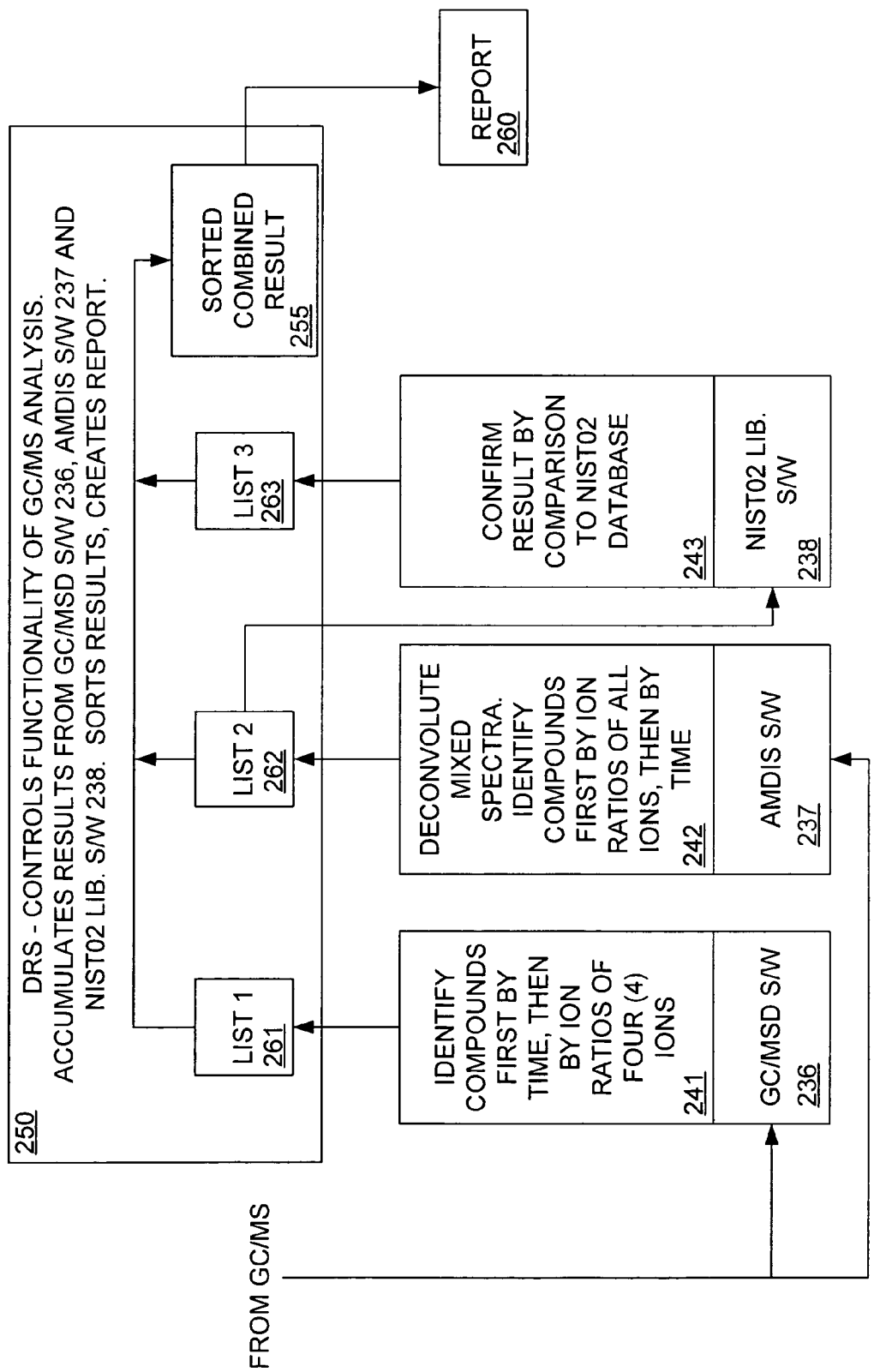
FIG. 5 is a functional block diagram illustrating the interaction among the deconvolution reporting software, the GC/MSD software, the AMDIS software and the NIST02 library software of FIG. 4.

FIG. 5 is a functional block diagram illustrating the interaction among the deconvolution reporting software 250, the GC/MSD software 236, the AMDIS software 237 and the NIST02 library software 238 of FIG. 4. The GC/MSD software 236 receives the results of the analysis performed by the GC/MS 110 (FIG. 3), identifies compounds first by time, then by ion (i.e., mass-to-charge "m/z") ratios using, in this example, four ions, and provides a first result 241 to the deconvolution reporting software 250. The deconvolution reporting software 250 receives the first result 241 and generates a corresponding first list 261. The first list 261 represents portions of the data contained in a TIC 20 and corresponds to the first result 241. The AMDIS software 237 also receives the results of the analysis performed by the GC/MS 110 (FIG. 3). The AMDIS software 237 deconvolutes the mixed spectra and identifies compounds first by ion ratios using a database containing complete ion identification criteria, and then by time. The AMDIS software 237 then provides a second result 242 to the deconvolution reporting software 250.

The deconvolution reporting software 250 receives the second result 242 and develops a second list 262 corresponding to the second result 242. The second list 262 is then provided to the NIST02 library software 238, which confirms the results by comparison to a NIST02 database, or library of target compounds. The NIST02 library software 238 then provides a third result 243 to the deconvolution reporting software 250. The deconvolution reporting software 250 receives the third result 243 and develops a third list 263, corresponding to the third result 243.

The deconvolution reporting software 250 combines the data from the first list 261, the second list 262, and the third list 263 into one report referred to as a sorted combined result 255. The sorted combined result 255 can be sorted by, for example, the retention time and the CAS number of the target compound. The sort can be performed in a fraction of the time that it would take an individual to analyze and verify the results provided by the GC/MSD software 236, the AMDIS software 237 and the NIST02 library software 238. The deconvolution reporting software 250 then generates a report 260 that can be sorted by, for example, the retention time or the CAS number of the target compound. A sample report 260 is illustrated below in FIG. 8.

Figures 6A, 6B:
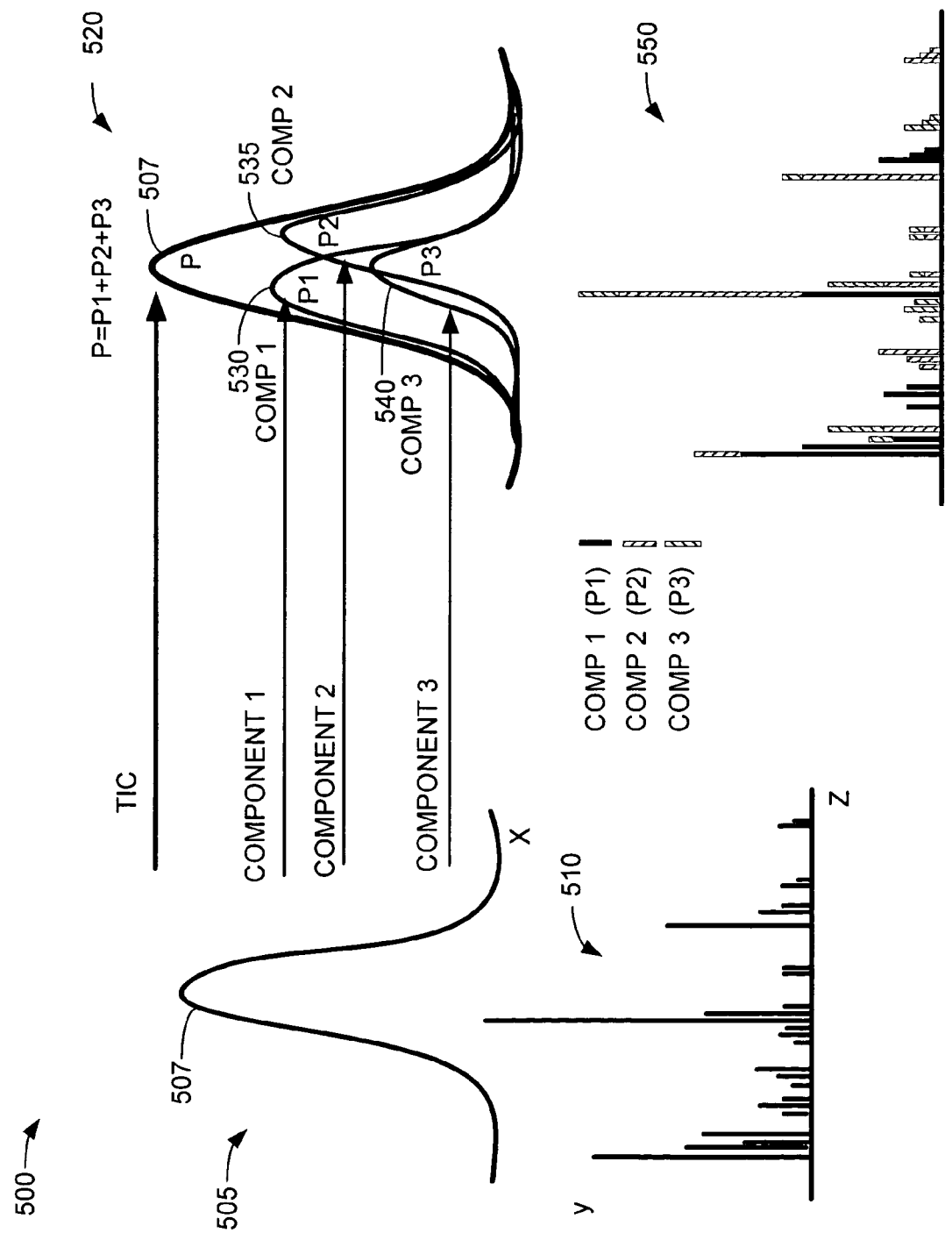
FIGS. 6A and 6B are a graphical representation collectively illustrating the total ion concentration and mass spectrum for a particular target sample.

FIGS. 6A and 6B are a graphical representation 500 collectively illustrating the total ion concentration and mass spectrum for a particular target sample. The graph 505 illustrates the total ion chromatogram having a peak 507. The peak 507 will likely include unresolved components in the sample. The mass spectrum 510 graphically illustrates the components that are present in the peak 507. In FIG. 6B, the peak 507 is illustrated as comprising three components, represented as peaks 530, 535, and 540. The peak 530 corresponds to a first component of the peak 507, the peak 535 corresponds to a second component of the peak 507, and the peak 540 corresponds to a third component of the peak 507. The mass spectrum 550 illustrated in FIG. 6B, includes compounds from the three peaks 530, 535 and 540. It is difficult to isolate and identify the separate components of the peak 507 when the compounds are not completely separated (i.e., resolved in time) as illustrated in FIG. 6B.

FIGS. 7A and 7B are a graphical representation 600 collectively illustrating the deconvolution of the peak "P" 507 of FIG. 6B into its constituent compounds. The peak 507, after being operated on by the AMDIS software 237 (FIGS. 4 and 5), is deconvoluted into peak 530 (peak 1), peak 535 (peak 2), and peak 540 (peak 3). The term deconvolution refers to a mathematical process that resolves unresolved compounds. Furthermore, the AMDIS software 237 resolves the peak 507 not only in time, but also by mass spectrum. This is illustrated by the individual mass spectra associated with each peak. For example, the mass spectrum 610 is associated with peak 530, the mass spectrum 620 is associated with the peak 535, and the mass spectrum 630 is associated with the peak 540. In this example, the peak 530 represents the sample matrix, the peak 535 represents matrix interference, and the peak 540 represents the target compound that is sought to be isolated. The three mass spectra 610, 620 and 630 are collectively shown in FIG. 7A as mass spectrum 550.

Figure 8:
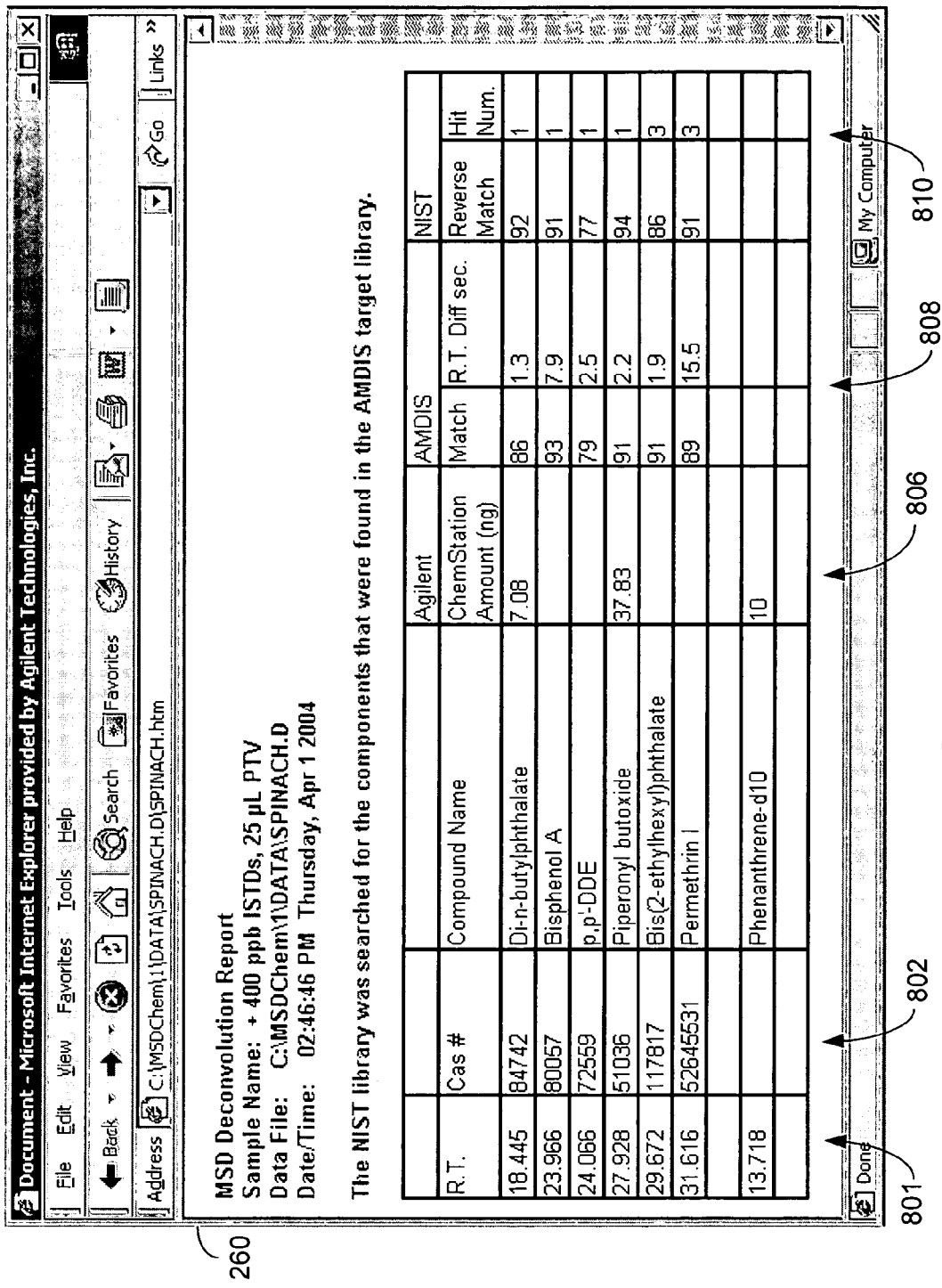
FIG. 8 is a graphical view illustrating a report generated by the deconvolution reporting software in accordance with an embodiment of the invention.

In accordance with an embodiment of the invention, the deconvolution reporting software 250 combines the results of the GC/MSD software 236, the AMDIS software 237, and the NIST02 library software 238 and automatically generates a sorted combined result 255 (FIGS. 4 and 5) and a report 260, an example of which is shown in FIG. 8.

FIG. 8 is a graphical view 800 illustrating a report 260 generated by the deconvolution reporting software 250. The deconvolution reporting software 250 combines the data from the GC/MSD software 236, the AMDIS software 237, and the NIST02 library software 238 into one report by building three lists 261, 262 and 263 (FIGS. 4 and 5) of results. The deconvolution software 250 then sorts the lists based on, for example, retention time and CAS number, generates the sorted combined result 255, and generates the report 260 shown in FIG. 8. For example, the report 260 can be sorted by retention time 801, or by CAS number 802. By combining the result of the GC/MSD software 236, shown in column 806, with the result from the AMDIS software 237, shown in column 808, and by combining the result from the NIST02 library software 238, shown in column 810, the report 260 can be sorted and can be used to verify target compounds in significantly less time than that required by manual operation to review the results 241, 242 and 243 (FIG. 4).

In an alternative application, the GC/MS 110 (FIG. 3) can also simultaneously acquire data from one or more additional GC detectors mounted on the GC/MS system. This data is represented as one or more signals additional to the TIC 20. The data are 2-dimensional, that is time and abundance only, no z-axis, and hence no ion data. The detectors are typically element specific, such as a dual flame photometric detector (DFPD) or an electron capture detector (ECD). An ECD detects compounds with halogen atoms present, such as chlorine, bromine, fluorine etc. This data can be used to further confirm the identity of a target compound. The report in FIG. 8 could be modified to include an additional column. For example, the entry "p,p'-DDE" contains chlorine and shows a response by ECD. That response could be noted in this additional column. If the ECD is calibrated, that response could be noted as an amount. Compounds that do not contain halogens would not show a response, hence the entries for those compounds would be blank in this additional column. As an additional benefit, the NIST02 search results, 810, could be further sorted to report only those compounds that showed a response dependent on the specific detector used.

Figure 9:
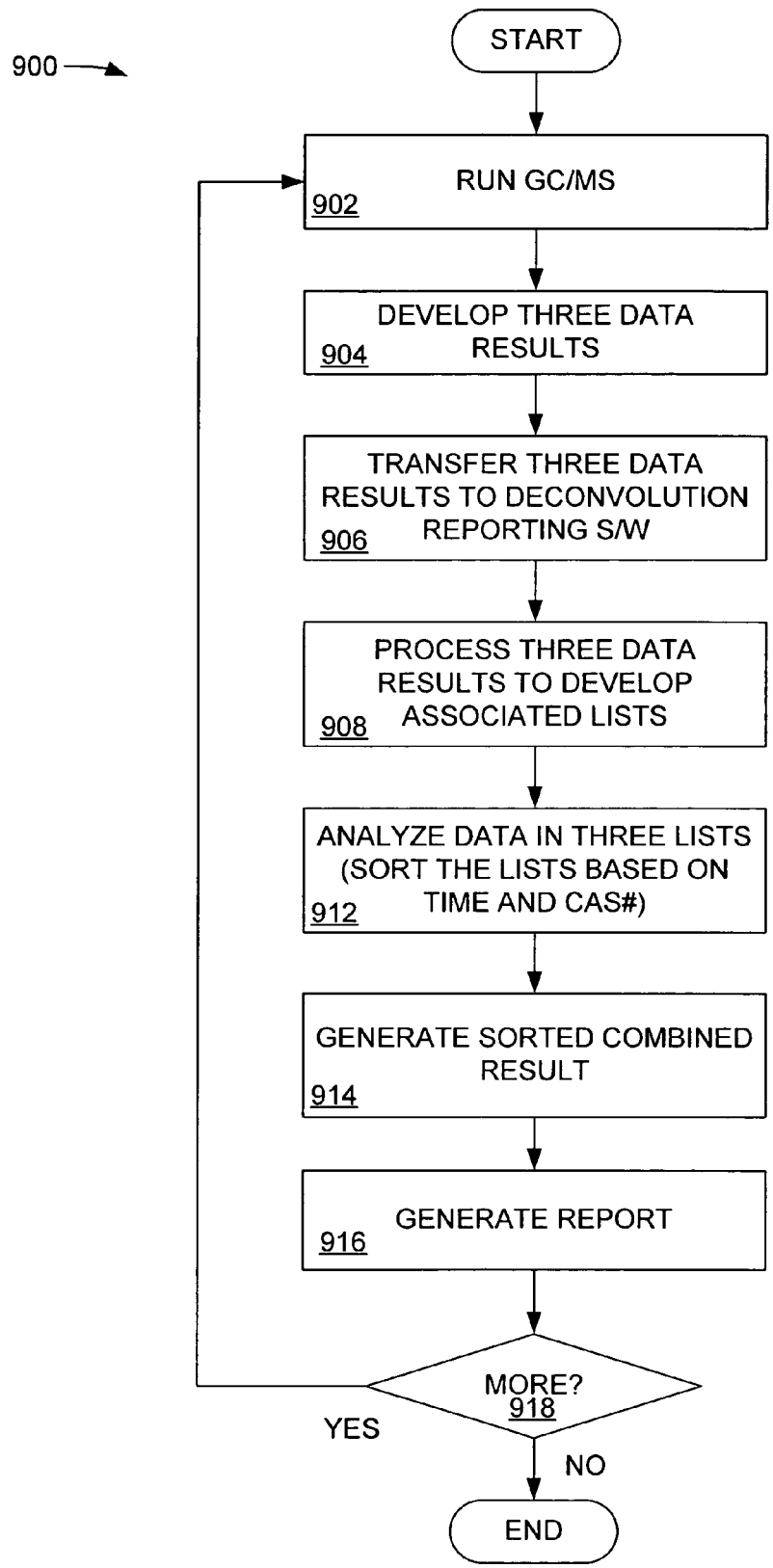
FIG. 9 is a flow chart describing the operation of one embodiment of the invention.

FIG. 9 is a flow chart 900 describing the operation of one embodiment of the invention. The blocks in the flowchart 900 illustrate the operation of one embodiment of the deconvolution reporting software 250. The blocks may be performed in the order shown, out of the order shown, or may be performed concurrently. In block 902 the gas chromatograph/mass spectrometer 110 is operated to detect, isolate and analyze target compounds. In block 904 the GC/MSD software 236, the AMDIS software 237, and the NIST02 library software 238 generate their respective results 241, 242 and 243. In block 906, the results 241, 242 and 243 are transferred to the deconvolution reporting software 250. In block 908, the deconvolution reporting software 250 generates lists 261, 262 and 263.

In block 912, the deconvolution reporting software 250 analyzes the data in the lists 261, 262 and 263 by, for example, sorting the lists 261, 262 and 263 based on retention time and/or CAS number. In block 914, the deconvolution reporting software 250 generates a sorted combined result 255. In block 916, the deconvolution reporting software 250 generates the report 260. In block 918, the deconvolution reporting software 250 determines whether additional samples are to be analyzed. If additional samples are to be analyzed, then the process returns to block 902. If it is determined in block 918 that no additional samples are to be analyzed, the process ends.

It will be apparent to those skilled in the art that many modifications and variations may be made to the preferred embodiments of the present invention, as set forth above, without departing substantially from the principles of the present invention. For example, the present invention can be used with a number of different GC/MS analysis devices and with a number of different liquid chromatograph/mass spectrometer (LC/MS) devices. All such modifications and variations are intended to be included herein within the scope of the present invention, as defined in the claims that follow.

What is claimed is:

1. A system for compound confirmation, comprising:
   a first software component configured to analyze a sample using time-based criteria and multiple ion comparison criteria to identify a target compound in the sample and to provide a first result;
   a second software component configured to analyze the sample by deconvolution of at least one peak having multiple co-eluting compounds and all ion criteria to identify the target compound in the sample and to provide a second result;
   a third software component configured to verify the identity of the target compound and to provide a third result; and
   a fourth software component configured to receive the first, second and third results and configured to automatically confirm the identity of the target compound by sorting the first, second and third results according to predefined criteria.

2. The system of claim 1, wherein the predefined criteria are chosen from retention time, four (4) ion analysis and chemical abstracts service (CAS) number.

3. The system of claim 2, further comprising a sorted combined result comprising data from the first, second and third results.

4. The system of claim 3, further comprising a report generated using the sorted combined result.

5. The system of claim 4, wherein the target compound is identified by a total ion chromatogram and the total ion chromatogram comprises the target compound and at least one additional compound, and the second software component isolates the target compound from the at least one additional compound in the total ion chromatogram, and the third software component automatically confirms the identity of the target compound.

6. A method for automatically identifying a compound, comprising:
   analyzing a sample using time-based criteria and multiple ion criteria to identify a target compound in the sample and to provide a first result;
   analyzing the sample by deconvoluting at least one peak having multiple co-eluting compounds and using all ion criteria to identify the target compound in the sample and to provide a second result;
   verifying the identity of the target compound and providing a third result; and
   receiving the first, second and third results and confirming the identity of the target compound by sorting the first, second and third results according to predefined criteria.

7. The method of claim 6, further comprising selecting the predefined criteria from retention time and chemical abstracts service (CAS) number.

8. The method of claim 7, further comprising generating a sorted combined result comprising data from the first, second and third results.

9. The method of claim 8, further comprising generating a report using the sorted combined result.

10. The method of claim 9, further comprising:
    identifying the target compound using a total ion chromatogram, wherein the total ion chromatogram comprises the target compound and at least one additional compound;
    isolating the target compound from the at least one additional compound in the total ion chromatogram; and
    automatically confirming the identity of the target compound.

11. A method for automatically verifying the existence of a target compound, comprising:
    generating a total ion chromatogram, the total ion chromatogram comprising a plurality of peaks, each peak representing one or more compounds in a sample matrix, each peak comprising at least two compounds;
    deconvoluting co-eluting compounds in each peak to isolate each target compound present in the peak; and
    automatically verifying the identity of each target compound against a target compound library.

12. The method of claim 11, further comprising generating a plurality of criteria identifying each target compound.

13. The method of claim 12, further comprising sorting each criteria to verify the identity of each target compound.

14. The method of claim 13, further comprising generating a sorted combined result identifying each target compound.

15. The method of claim 14, further comprising generating a report capturing the sorted combined result.

16. The method of claim 15, wherein the plurality of criteria comprises retention time and four (4) ion data.

* * * * *

UNITED STATES PATENT AND TRADEMARK OFFICE
CERTIFICATE OF CORRECTION

| | | |
|---|---|---|
| PATENT NO. | : 7,117,103 B2 | Page 1 of 1 |
| APPLICATION NO. | : 10/859843 | |
| DATED | : October 3, 2006 | |
| INVENTOR(S) | : Szelewski et al. | |

It is certified that error appears in the above-identified patent and that said Letters Patent is hereby corrected as shown below:

On the Title page, in "Assistant Examiner", in column 2, line 1, after "Tung" insert -- S. --.

In column 10, line 49-50 (Approx.), in Claim 11, delete "deconvoluting co-eluting compounds in each peak to isolate each target compound present in the peak; and" and insert -- deconvoluting at least one peak having multiple co-eluting compounds to isolate each target compound present in the at least one peak; and --, therefor.

Signed and Sealed this

Twentieth Day of March, 2007

JON W. DUDAS
*Director of the United States Patent and Trademark Office*